United States Patent
Wang et al.

(10) Patent No.: US 10,351,856 B2
(45) Date of Patent: Jul. 16, 2019

(54) RIBONUCLEIC ACID APTAMER HAVING INHIBITORY EFFECT ON NON-SMALL CELL LUNG CANCER AND PHARMACEUTICAL COMPOSITION COMPRISING SAME

(71) Applicant: BIOPHARMAGEN CORP., FANGZHOU SUZHOU, Suzhou (CN)

(72) Inventors: Hanlu Wang, Suzhou (CN); Rihe Liu, Suzhou (CN); Yongping Jiang, Suzhou (CN)

(73) Assignee: BIOPHARMAGEN CORP., FANGZHOU SUZHOU, Suzhou (CN)

( * ) Notice: Subject to any disclaimer, the term of this patent is extended or adjusted under 35 U.S.C. 154(b) by 0 days.

(21) Appl. No.: 16/085,861

(22) PCT Filed: Mar. 23, 2017

(86) PCT No.: PCT/CN2017/077813
§ 371 (c)(1),
(2) Date: Sep. 17, 2018

(87) PCT Pub. No.: WO2017/162185
PCT Pub. Date: Sep. 28, 2017

(65) Prior Publication Data
US 2019/0030174 A1    Jan. 31, 2019

(30) Foreign Application Priority Data
Mar. 23, 2016    (CN) .......................... 2016 1 0168486

(51) Int. Cl.
| | | |
|---|---|---|
| *C12N 15/11* | (2006.01) | |
| *C12N 15/115* | (2010.01) | |
| *A61K 31/7105* | (2006.01) | |
| *A61K 47/69* | (2017.01) | |
| *A61K 47/54* | (2017.01) | |
| *A61P 35/00* | (2006.01) | |
| *A61K 9/127* | (2006.01) | |
| *A61K 31/282* | (2006.01) | |
| *A61K 31/337* | (2006.01) | |
| *A61K 31/4355* | (2006.01) | |
| *A61K 31/7068* | (2006.01) | |

(52) U.S. Cl.
CPC .......... *C12N 15/115* (2013.01); *A61K 9/1271* (2013.01); *A61K 31/282* (2013.01); *A61K 31/337* (2013.01); *A61K 31/4355* (2013.01); *A61K 31/7068* (2013.01); *A61K 31/7105* (2013.01); *A61K 47/555* (2017.08); *A61K 47/6911* (2017.08); *A61P 35/00* (2018.01); *C12N 2310/16* (2013.01); *C12N 2310/321* (2013.01)

(58) Field of Classification Search
None
See application file for complete search history.

(56) References Cited

U.S. PATENT DOCUMENTS

2003/0055014 A1* 3/2003 Bratzler ............. A61K 31/7088
514/44 R
2009/0081675 A1* 3/2009 Colston, Jr. ............ C12Q 1/689
435/6.18

FOREIGN PATENT DOCUMENTS

WO    WO-2012078637 A2 *    6/2012    ........... C12N 15/111

OTHER PUBLICATIONS

Alibolandi et al, In vitro and in vivo evaluation of therapy targeting epithelial-cell adhesion-molecule aptamers for non-small cell lung cancer, Journal of Controlled Release, Apr. 2015, 209: 88-100 (Year: 2015).*

* cited by examiner

*Primary Examiner* — Ekaterina Poliakova-Georgantas
(74) *Attorney, Agent, or Firm* — CBM Patent Consulting, LLC (57) ABSTRACT

It relates to a ribonucleic acid aptamer having an inhibitory effect on non-small cell lung cancer and a pharmaceutical composition comprising the same. The ribonucleic acid aptamer can bind to human non-small cell lung cancer in vivo or in vitro with high specificity and high affinity to achieve an effect of inhibiting non-small cell lung cancer; and the ribonucleic acid aptamer can also be linked, coupled or polymerized with other non-small cell lung cancer therapeutic drugs to achieve a more excellent effect of inhibiting non-small cell lung cancer.

8 Claims, 4 Drawing Sheets

Specification includes a Sequence Listing.

RIBONUCLEIC ACID APTAMER HAVING INHIBITORY EFFECT ON NON-SMALL CELL LUNG CANCER AND PHARMACEUTICAL COMPOSITION COMPRISING SAME

TECHNICAL FIELD

The present invention belongs to the field of biotechnology, and more particularly, to a ribonucleic acid aptamer having an inhibitory effect on non-small cell lung cancer and a pharmaceutical composition comprising the same.

BACKGROUND ART

Cancer has become one of the leading causes of death in the world's population. According to statistics, six people die every minute from cancer in China. Among them, lung cancer is a malignant disease with the No. 1 morbidity and mortality worldwide and throughout China. At present, surgical resection and conventional chemotherapy are commonly used in clinical practice, but the high recurrence rate and side effects of surgery and chemotherapy have always been clinical problems to be solved. It is urgent to employ new methods and means to treat patients with lung cancer and extend the lifetime of the patients. An aptamer is a single-stranded oligonucleotide sequence (ssDNA, RNA or modified RNA) that can be folded into a specific three-dimensional structure and specifically bound to a target by a spatial configuration. Since aptamers have the specificity to bind their targets, some of the aptamers can also inhibit the function of the target substance and block the signaling pathway in the cell by binding to the target, and thus, have the value to further develop a nucleic acid drug for specifically inhibiting the target.

Epirubicin (EPI) is a broad-spectrum chemotherapeutic drug used in the treatment of a variety of cancers (such as acute leukemia, malignant lymphoma, breast cancer, bronchial lung cancer, ovarian cancer, lung cancer, bladder cancer, stomach cancer, liver cancer and other solid tumors). Its mechanism of action is to directly intercalate into DNA base pairs, interfere with the transcription process, prevent the formation of mRNA, and thus inhibit the synthesis of DNA and RNA. It is a cell cycle non-specific drug and is effective for a variety of transplanted tumors. However, epirubicin is not specific for cell toxicity, and it can cause damage to other organs while killing tumor cells, affecting patient tolerance and therapeutic effects. Therefore, it is of great significance to develop a targeted drug that can carry cytotoxic drugs such as epirubicin, and perform targeted killing on tumors and reduce damage to other cells.

The aptamer is a short single-stranded DNA or RNA molecule with recognition activity evolved from systematic evolution of ligands by exponential enrichment (SELEX), which is a manual screening technique simulating the natural evolution process. It can be folded into a specific three-dimensional structure to bind to the target, and has the characteristics of high affinity, high specificity, no immunogenicity, easy synthesis, in vitro modification, good stability and the like. Some of the aptamers not only can bind to the target substance, but also can inhibit the function of target molecules, and show broad application prospects in the targeted treatment of diseases. Up to now, FDA has approved a nucleic acid aptamer specific for VEGF developed by Eyetch/Pfizer, pegaptanib sodium (trade name Macugen), for the treatment of age-related macular degeneration. In addition, in the field of tumor therapy, aptamers targeting VEGF, E2F, nucleolin and the like have also entered clinical research pipelines, revealing the prospect of nucleic acid aptamers in tumor therapy.

Although the SELEX technique has been applied to screening nucleic acid aptamers, the development and screening of aptamers that are truly useful remain very difficult in the art, and there are still very few aptamers that currently have binding ability or inhibitory effects on specific cancers.

SUMMARY OF THE INVENTION

The objective of the present invention is to provide a ribonucleic acid aptamer having an inhibitory effect on non-small cell lung cancer and a pharmaceutical composition comprising the same.

In the first aspect, the present invention provides a pharmaceutical composition comprising a ribonucleic acid aptamer, the pharmaceutical composition comprising a ribonucleic acid aptamer (preferably, the amount of which is an effective amount), and a pharmaceutically acceptable carrier;

wherein, the nucleic acid aptamer is selected:
(1) a ribonucleic acid aptamer having a nucleotide sequence as shown in SEQ ID NO: 1; or
(2) a ribonucleic acid aptamer capable of hybridizing with a nucleotide sequence shown in SEQ ID NO: 1 under stringent conditions and having a function of specifically binding to human non-small cell lung cancer cells; or
(3) a ribonucleic acid aptamer having 80% or more (preferably 85% or more; more preferably 90% or more; further preferably 95% or more) identity with the nucleotide sequence shown in SEQ ID NO: 1 and having a function of specifically binding to human non-small cell lung cancer cells; or
(4) a ribonucleic acid aptamer being a truncation of the nucleotide sequence shown in SEQ ID NO: 1 and having a function of specifically binding to human non-small cell lung cancer cells; or
(5) a ribonucleic acid aptamer having a nucleotide sequence complementary to a nucleotide sequence of the ribonucleic acid aptamer defined by any one of (1) to (4).

In a preferred embodiment, the pharmaceutical composition further comprises an antitumor drug linked, coupled or polymerized with the ribonucleic acid aptamer.

In another preferred embodiment, in the pharmaceutical composition, the antitumor drug is a tumor-inhibiting chemotherapeutic drug, a tumor-inhibiting nucleic acid (for example, an interfering molecule that specifically inhibits a tumor-associated gene, such as siRNA), or a tumor-inhibiting protein (such as an antibody that specifically inhibits tumor-associated proteins).

In a preferred embodiment, the chemotherapeutic drug includes, but is not limited to, epirubicin, doxorubicin, carboplatin, cisplatin, paclitaxel, docetaxel and gemcitabine.

In a preferred embodiment, the chemotherapeutic drug is epirubicin, and the ribonucleic acid aptamer is adducted with epirubicin, the molar ratio of the ribonucleic acid aptamer to the epirubicin in the adduct being 1:(2-20); preferably 1:(4-12); and more preferably 1:(7-9).

In a preferred embodiment, the ribonucleic acid aptamer is a modified ribonucleic acid aptamer having a half-life longer than an unmodified ribonucleic acid aptamer, or a higher stability than the unmodified ribonucleic acid aptamer; and preferably, the modified ribonucleic acid aptamer is:
- a modified ribonucleic acid aptamer obtained by linking a ribonucleic acid aptamer to PEG;
- a ribonucleic acid aptamer embedded in a PEG-liposome mixture;
- a nucleic acid aptamer with 2'F modified U and C bases;
- a nucleic acid aptamer with 2'OMe modified bases; or
- a biotin modified nucleic acid aptamer.

In another aspect, the present invention provides a modified ribonucleic acid aptamer, the modified ribonucleic acid aptamer being:
- a modified ribonucleic acid aptamer obtained by linking a ribonucleic acid aptamer to PEG;
- a ribonucleic acid aptamer embedded in a PEG-liposome mixture;
- a nucleic acid aptamer with 2'F modified U and C bases;
- a nucleic acid aptamer with 2'OMe modified bases; or
- a biotin modified nucleic acid aptamer.

In another aspect, the present invention provides an adduct inhibiting non-small cell lung cancer, the adduct comprising a ribonucleic acid aptamer and a chemotherapeutic drug, which are coupled, attached or polymerized to each other; preferably, the chemotherapeutic drug includes, but is not limited to, epirubicin, doxorubicin, carboplatin, cisplatin, paclitaxel, docetaxel and gemcitabine.

In another aspect, the present invention provides application of the above-mentioned pharmaceutical composition, the modified ribonucleic acid aptamer, or the adduct in the preparation of a kit for inhibiting non-small cell lung cancer.

In another aspect, the present invention provides a kit for inhibiting non-small cell lung cancer, the kit comprising:
- the pharmaceutical composition; or
- the modified ribonucleic acid aptamer; or
- the adduct.

Other aspects of the present invention will be apparent to those skilled in the art from this disclosure.

DETAILED DESCRIPTION OF THE INVENTION

The inventors screened out a targeting ribonucleic acid aptamer named RA16 by an in vivo-SELEX method. It can bind to human non-small cell lung cancer in vivo or in vitro with high specificity and high affinity to achieve an effect of inhibiting non-small cell lung cancer; and it can also be linked, coupled or polymerized with other non-small cell lung cancer therapeutic drugs to achieve a more excellent effect of inhibiting non-small cell lung cancer. The present invention is completed on such a basis.

Ribonucleic Acid Aptamer RA16

The ribonucleic acid aptamer RA16 of the present invention has a nucleotide sequence as shown in SEQ ID NO: 1. The ribonucleic acid aptamer of the present invention is in the form of RNA. The full-length nucleotide sequence of the ribonucleic acid aptamer of the present invention or a segment thereof can usually be obtained by in vitro transcription, recombination or chemical synthesis.

Hybridization of polynucleotides is a technique well known to those skilled in the art, and the hybridization characteristics of a particular pair of nucleic acids indicate their similarity or identity. Therefore, the present invention also encompasses a polynucleotide which hybridizes with the nucleotide sequence of the ribonucleic acid aptamer of the present invention and which has at least 70%, more preferably at least 80% (for example, 85%, 90%, 95%, 96%, 97%, or 98%), identity with the nucleotide sequence of the ribonucleic acid aptamer of the present invention, the nucleic acid also having the function of specifically binding to human non-small cell lung cancer cells.

Sequence "identity" refers to the percentage of the same corresponding bases by position, and can indicate a similarity level (also known as sequence homology, similarity or identity) between two or more nucleic acids.

The present invention particularly relates to polynucleotides hybridizable with the polynucleotides of the present invention under stringent conditions. "Stringent conditions" means: (1) hybridization and elution at lower ionic strength and higher temperature, for example 0.2×SSC, 0.1% SDS, 60° C.; or (2) during hybridization, addition of a denaturant, such as 50% (v/v) formamide, 0.1% calf serum/0.1% Ficoll, 42° C., etc.; or (3) hybridization occurs only when the identity between the two sequences is at least 70% or more, 75% or more, 80% or more, 85% or more or 90% or more, more preferably 95% or more. Moreover, the hybridizable polynucleotides also have the function of specifically binding to human non-small cell lung cancer cells.

Studies by the inventors show that the ribonucleic acid aptamer RA16 is capable of binding human non-small cell lung cancer in vitro and in vivo with high specificity and high affinity. In vitro and in vivo studies further found that RA16 can specifically, remarkably and directly inhibit the proliferation of human non-small cell lung cancer H460 cells; the direct inhibition of RA16 on H460 cells is dose-dependent, with an IC50 of 116.7 nM; and during treatment with RA16 at a concentration of 300 nM or higher, the inhibition rate for H460 cell growth can reach 70% or more, while it has no inhibitory effect on other tumor cells such as human cervical cancer Hela cells. At the same time, the ribonucleic acid aptamer RA16 can also inhibit the growth of human non-small cell lung cancer transplanted tumors in the tumor-bearing mice. When the H460 transplanted tumor model mice are treated with RA16, the tumor growth rate is significantly slower than that of the control group, and the inhibition rate of tumor growth reaches 54.3% during the 16-day observation period.

The inventors have found for the first time that the ribonucleic acid aptamer RA16 of the present invention can specifically and remarkably inhibit the proliferation of non-small cell lung cancer cells, but has no inhibitory effect on other tumor cells such as human cervical cancer HeLa cells; and the ribonucleic acid aptamer RA16 can also inhibit the growth of non-small cell lung cancer transplanted tumors in tumor-bearing mice. Therefore, the ribonucleic acid aptamer RA16 will provide a new strategy for the treatment of non-small cell lung cancer.

Modified Ribonucleic Acid Aptamer RA16

The present invention also relates to a ribonucleic acid aptamer modified based on the ribonucleic acid aptamer, for example, in order to increase the stability of the ribonucleic acid aptamer or the effective acting time in vivo (e.g., increase half-life), some chemical modifications are made on a portion of the bases at both ends or at the middle of the sequence.

As a preferred manner of the present invention, the nucleic acid is modified for the purpose of increasing half-life. Such modified ribonucleic acid aptamers include, for example, a modified ribonucleic acid aptamer obtained by linking a ribonucleic acid aptamer with PEG; a ribonucleic acid aptamer embedded in a PEG-liposome mixture, or the like. Although the inventors have provided a preferred modification manner, it will be appreciated that other modified nucleic acids that have been used in the art may also be employed in the present invention in a modification manner that increases the half-life or stability.

Adduct Containing Ribonucleic Acid Aptamer RA16

The present invention also relates to an adduct containing the ribonucleic acid aptamer RA16. Typically, the adduct comprises the ribonucleic acid aptamer and an antitumor drug linked, coupled or polymerized with the ribonucleic acid aptamer. The present inventors have found that after the ribonucleic acid aptamer and some antitumor drugs form into an adduct, the targeting activity of the ribonucleic acid aptamer has not been changed, so that the antitumor drug can also reach the tumor site of non-small cell lung cancer and exert an inhibitory effect together with the ribonucleic acid aptamer.

The antitumor drug is generally a drug having an inhibitory effect on non-small cell lung cancer, and the antitumor drug is capable of relatively stable linking (including coupling) with the nucleic acid. The therapeutic drug includes, for example, a chemotherapeutic drug, a small molecule compound (such as a chemotherapeutic drug) that inhibits human non-small cell lung cancer, a nucleic acid drug (such as siRNA or shRNA) or a protein drug. The therapeutic drug itself may not have the targeting activity to human non-small cell lung cancer, but it can well reach the non-small cell lung cancer site by linking, coupling or polymerization with the ribonucleic acid aptamer of the present invention. Although not enumerated, some antitumor drugs which can be expected to be linked, coupled or polymerized with the ribonucleic acid aptamer of the present invention can be used in the present invention.

As a preferred manner of the present invention, the antitumor drug is a chemotherapeutic drug, such as epirubicin, doxorubicin, carboplatin, cisplatin, paclitaxel, docetaxel, gemcitabine or the like.

In a preferred embodiment of the present invention, epirubicin is adducted with the ribonucleic acid aptamer, and the epirubicin can be embedded into the nucleic acid sequence of the ribonucleic acid aptamer to form an adduct (RNA-EPI adduct). In the adduct, the molar ratio of the ribonucleic acid aptamer to the epirubicin is 1:(2-20); preferably 1:(4-12); and more preferably 1:(7-9).

The RNA-EPI adduct can efficiently inhibit the proliferation of human non-small cell lung cancer (inhibition rate of 93.6%) in vitro, and can reduce the cytotoxicity of epirubicin on other tumor cells. In more in-depth in vivo experiments, when RA16-EPI was used in the treatment of human non-small cell lung cancer H460 transplanted tumor mouse model, the tumor growth rate was significantly slower than that of the control group, and in the 16-day observation period, the inhibition rate of the high-dose group reached 64.38%, which was 17.25% higher than that of the high-dose EPI group (47.13%) alone.

Therefore, the inventors disclose for the first time a strategy for forming an adduct of ribonucleic acid aptamer RA16 and EPI for the treatment of human non-small cell lung cancer. The RNA-EPI adduct is capable of efficiently inhibiting proliferation of human non-small cell lung cancer in vitro and in vivo. The RNA-EPI adduct has a stronger inhibitory effect on inhibiting human non-small cell lung cancer than EPI or aptamer RA16 alone, and reduces the cytotoxicity for other tumor cells, revealing a selective synergistic inhibitory effect of the RA16-EPI adduct on human non-small cell lung cancer.

Pharmaceutical Composition

Based on the novel findings of the inventors, the present invention provides a pharmaceutical composition comprising the ribonucleic acid aptamer, comprising: an effective amount of the ribonucleic acid aptamer, and a pharmaceutically acceptable carrier. As a preferred manner of the present invention, the ribonucleic acid aptamer may be the above-mentioned modified ribonucleic acid aptamer RA16; alternatively, the pharmaceutical composition comprising the ribonucleic acid aptamer comprises an adduct of an effective amount of the ribonucleic acid aptamer RA16 linked, coupled or polymerized with other antitumor drugs.

The term "pharmaceutically acceptable" means that when the molecular body and composition are suitably administered to an animal or a human, they do not produce an adverse, allergic or other untoward reaction.

Specific examples of some substances which can be used as pharmaceutically acceptable carriers or components thereof are sugars, such as lactose, glucose and sucrose; starches, such as corn starch and potato starch; cellulose and derivatives thereof, such as sodium carboxymethyl cellulose, ethyl cellulose and methyl cellulose; gum tragacanth powder; malt; gelatin; talc; solid lubricants, such as stearic acid and magnesium stearate; calcium sulfate; vegetable oils, such as peanut oil, cottonseed oil, sesame oil, olive oil, corn oil and cocoa butter; polyols, such as propylene glycol, glycerol, sorbitol, mannitol and polyethylene glycol; alginic acid; emulsifiers, such as Tween®; wetting agents, such as sodium lauryl sulfate; coloring agents; flavoring agents; tableting agents, stabilizers; antioxidants; preservatives; pyrogen-free water; and isotonic saline solutions and phosphate buffers, and the like.

When a pharmaceutical composition is used, a safe and effective amount of the pharmaceutical composition of the present invention is administered to a subject in need of treatment. The term "effective amount" refers to an amount that can exert the pharmaceutical activity of the ribonucleic acid aptamer (or antitumor drugs linked, coupled or polymerized therewith) for a subject receiving the drug.

Depending on different subjects, such an effective amount will generally be an amount that can be assessed by one skilled in the art or by a clinician depending on the type, age, weight and approximate disease condition of the subject, administration manner, and the like. Of course, specific doses should also consider factors such as the route of administration, the health of the patient, etc., which are within the skill of the skilled physician.

The present invention further relates to a kit for inhibiting non-small cell lung cancer, comprising: the above-mentioned pharmaceutical composition of the present invention;

or the above-mentioned modified ribonucleic acid aptamer; or the above-mentioned adduct. In order to facilitate the application of the clinician and the subject, the kit may also include instructions for use or instructions for the drug.

The present invention is further illustrated below in conjunction with specific embodiments. It should be understood that these embodiments are not intended to limit the scope of the present invention. The experimental methods in the following embodiments which do not specify the specific conditions are generally in accordance with conventional conditions, such as conditions in J. Sambrook et al., Molecular cloning—Laboratory manuals, Third Edition, Science Press, 2002, or the conditions recommended by the manufacturer.

Figure 1:
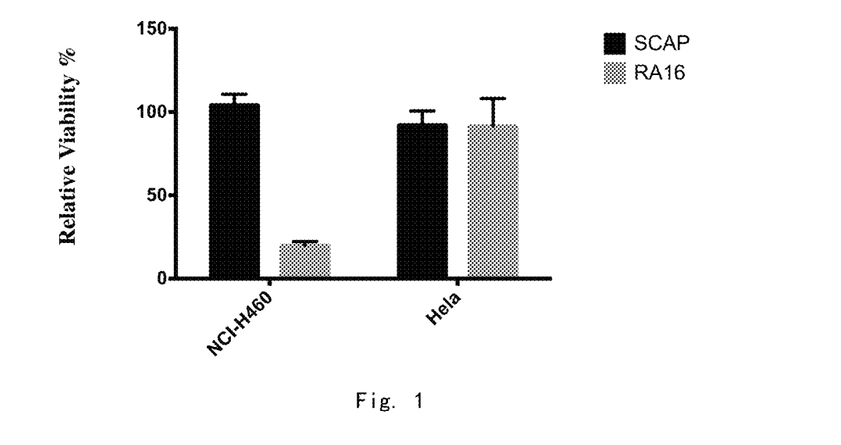
FIG. 1: The relative cell viability of NCI-H460 cells and Hela cells respectively treated with 300 nM SCAP and RA16 for 48 hours are detected by a CCK-8 method. SCAP is a nucleic acid obtained by randomly shuffling the sequence of RA16.

Embodiment 1: Inhibitory Effect of RA16 on Human Non-Small Cell Lung Cancer Cell Lines In order to clarify the effect of the nucleic acid aptamer RA16 on the proliferation of human non-small cell lung cancer cell lines, the inventors used the CCK-8 method (CCK-8 kit purchased from Dojindo Molecular Technologies, Inc.) to detect the relative viability of human non-small cell lung cancer cell line H460 (ATCC) and other tumor cells (human cervical cancer Hela cells) (the initial cell concentration was $2 \times 10^4$ cells/ml) after 48 h of treatment by 300 nM RA16. The same treatment was performed as the control with the same concentration of SCAP obtained by randomly shuffling the RA16. After three independent experiments, it was found that RA16 treatment could obviously inhibit the proliferation of human non-small cell lung cancer cell line H460, but have no obvious effects on other tumor cells, as shown in FIG. 1.

The sequence of RA16 is:

```
                                        (SEQ ID NO: 1)
5'-GGGAGAGAACAAUGACCUGCGGUGCCAAGCCGUCGGGUUAUGUUGAU

CUCCACAAGGACGAGUGCAUUGCAUCACGUCAGUAG-3';
```

RA16 was prepared by in vitro transcription, in which 2-F-modified U and C bases were incorporated, and all of the U and C bases were 2'F modified in the obtained RA16 RNA sequence.

The sequence of SCAP is:

```
                                        (SEQ ID NO: 2)
5'-GGGAGAGAACAAUGACCUGUUGCAAGCGCGUCGGUAAUUCGCGCACA

UGGCAGGCUUCUGAGUGCAUUGCAUCACGUCAGUAG-3';
```

In the same manner as the preparation method of RA16, the RNA sequence of SCAP was prepared, and all UC bases were subjected to 2'F modification.

Figure 2A:
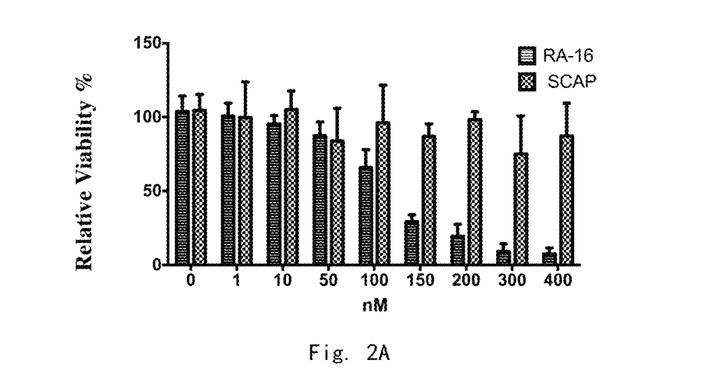
FIG. 2A: The dose-dependent inhibitory effect of RA16 (concentrations 0, 5, 10, 50, 100, 150, 200, 300, 400 nM) on H460 is detected using the CCK-8 method. The same concentrations of SCAP is used as a control.
Figure 2B:
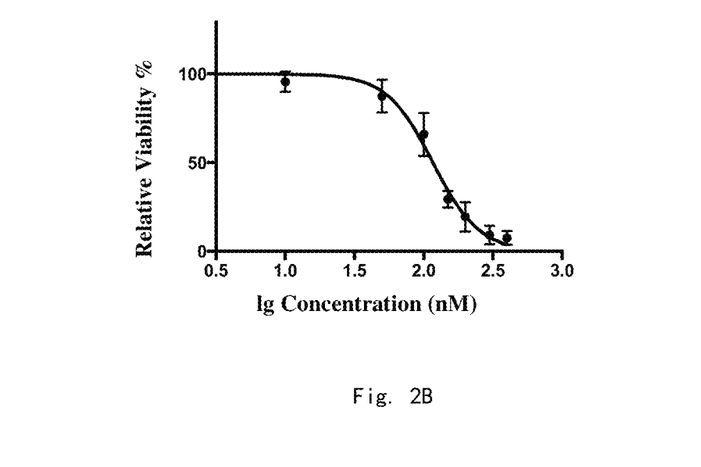
FIG. 2B: The dose-dependent inhibitory effect of Ig.

Further, CCK-8 assay was used to detect the growth conditions of human non-small cell lung cancer H460 cells and human cervical cancer Hela cells (the concentration of test cells was about $2 \times 10^4$/ml) after 48 hours of treatment with different concentrations of nucleic acid aptamer RA16 and SCAP (concentration 0, 5, 10, 50, 100, 150, 200, 300, 400 nM respectively) with randomly srambled RA16, and after three independent experiments, the results are shown in FIG. 2A-B.

The results showed that RA16 could inhibit the proliferation of H460 cells in a dose-dependent manner with an IC50 value of 116.7 nM (In general, IC50 values below 10 µM at the cellular level have antitumor drug development potential, and the smaller the IC50 value concentration indicating the better the inhibitory effect). During treatment by RA16 with a concentration of 300 nM or more, the inhibition rate of cell growth was 75% or more, and the randomly scrambled RA16 sequence had little effect on the proliferation of H460 cells.

Meanwhile, RA16 had no significant effect on human cervical cancer Hela cells, revealing the specificity of the inhibitory effect of RA16 on human non-small cell lung cancer cell lines.

Embodiment 2: Preparation of RA16-EPI Adduct 2.1 Preparation of RA16 by In Vitro Transcription In vitro transcription reaction was carried out using DNA-16 as the template and 2'F-dCTP, 2'F-dUTP, GTP, ATP and amino-GMP as substrates. The reaction conditions were: 37° C., 8 h.

The sequence of DNA-16 is as follows:

```
                                        (SEQ ID NO: 3)
5'-CACTAATACGACTCACTATAGGGAGAGAACAATGACCTGCGGTGCCA

AGCCGTCGGGTTATGTTGATCTCCACAAGGACGAGTGCATTGCATCACGT

CAGTAG-3'.
```

After completion of the reaction, the DNA template was removed with DNase I, and purified RA16 was obtained by phenol/chloroform extraction and ethanol precipitation.

2.2 PEGylation

The ethanol-precipitated RNA (i.e. RA16) was suspended in 100 µL of DEPC-H$_2$O, an equal volume of 0.2M NaHCO$_3$ solution was added, together with an appropriate amount of NHS-PEG (30 kD) dry powder. The reaction was carried out for 2 h at room temperature, and a Tris-HCl buffer with the final concentration of 20 mM was added to neutralize the unreacted NHS to obtain PEGylated RA16. Purified PEG-modified RA16 was obtained by phenol/chloroform extraction and ethanol precipitation. The 5' end of the RNA was PEGylated.

2.3 Preparation of RA16-EPI Adduct

The ethanol-precipitated RNA (i.e. RA16) was suspended in 100 µL HBS solution, and after treating at 95° C. for 3 min, the reaction was cooled to room temperature such that the RNA recovered to a uniform secondary structure. An epirubicin (EPI) solution was added at a molar ratio of 1:8, and the mixture was incubated for 1 hour at room temperature to form an adduct of RA16 and EPI. In the polymer, EPI was intercalated into the GC pairs of the RNA structure.

2.4 Preparation of PEGylated RA16-EPI Adduct

The PEG-modified RA16 and epirubicin were dissolved in an HBS buffer at a molar ratio of 1:8, and allowed to stand in the dark at room temperature for 2 h to obtain the PEGylated RA16-EPI adduct.

Figure 3:
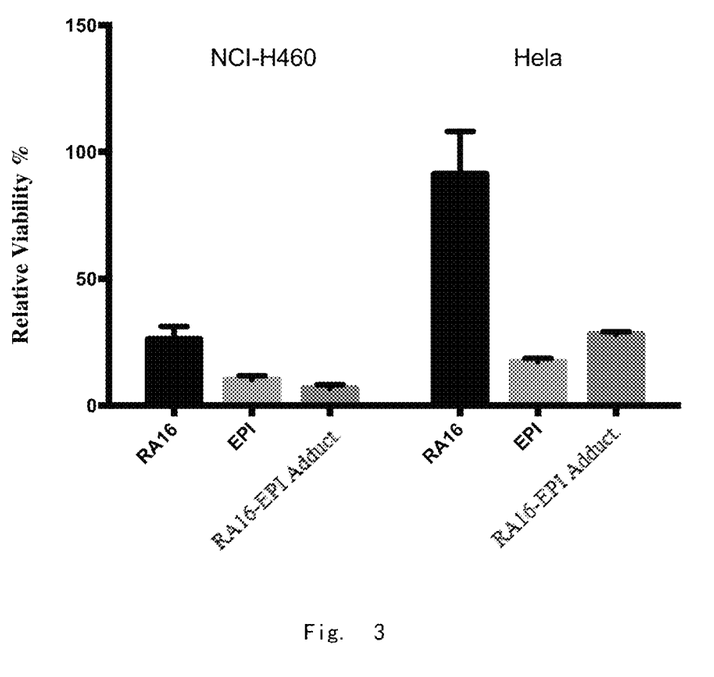
FIG. 3: The inhibitory activities of the RA16-EPI adduct on H460 and Hela cells are detected by the CCK-8 method.

Embodiment 3: Inhibitory Effect of RA16-EPI Adduct on Human Non-Small Cell Lung Cancer Cell Lines In order to clarify the effect of the nucleic acid aptamer RA16-EPI adduct on the proliferation of human non-small cell lung cancer cell lines, the inventors used the CCK-8 method to detect the relative viability of human non-small cell lung cancer cell line H460 and other tumor cell lines (human cervical cancer Hela cells) (initial cell concentration was $2 \times 10^4$ cells/ml) after 48 h of treatment by 375 nM RA16-EPI. After three independent repeated experiments, it was found that RA16-EPI treatment could obviously inhibit the proliferation of human non-small cell lung cancer cell line H460, and its inhibitory effect on human non-small cell lung cancer was further enhanced by using the same concentration of RA16 or EPI alone, as shown in FIG. 3.

At the same time, the RA16-EPI also had an inhibitory effect on human cervical cancer Hela cells (FIG. 3), revealing the selectivity and targeting activity of RA16 for human non-small cell lung cancer and human cervical cancer cell line, and suggesting that the inventors applied the RA16-EPI adduct to the clinic to significantly reduce the toxicity and damage of chemotherapeutic drugs to other tissues and organs.

Embodiment 4: Inhibitory Effect of RA16 on Human Non-Small Cell Lung Cancer (In Vivo)

Figure 4:
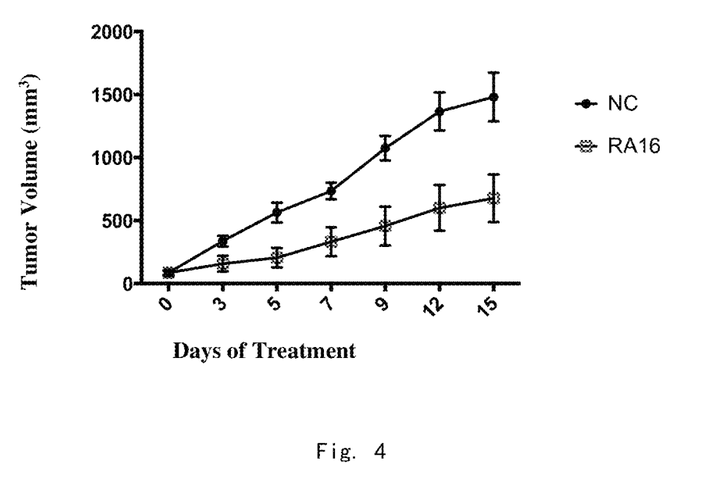
FIG. 4: A tumor growth curve for evaluating the efficacy of RA16 on tumor growth in tumor-bearing mice. NC represents a negative control group.

In order to clarify the effect of the nucleic acid aptamer RA16 on the growth of human non-small cell lung cancer solid tumors, the inventors used model mice that were injected with human non-small cell lung cancer H460 cells and constructed with a subcutaneous tumor as experimental subjects (initial mean tumor volume was 100 mm$^3$ or so). They were randomly divided into two groups, each of which had 6 tumor-bearing mice. One group served as a negative control group (0.1 ml of normal saline was injected intravenously on the $0^{th}$, $3^{rd}$, $5^{th}$, $7^{th}$, and $9^{th}$ days respectively); and the other was an RA16 treatment group (2 nmol of RA16 was injected intravenously the $0^{th}$, $3^{rd}$, $5^{th}$, $7^{th}$, and $9^{th}$ days respectively). Every other day, the tumor diameter of the tumor-bearing mice was measured, the tumor volume was calculated, and the tumor growth curves were drawn (FIG. 4). On the $16^{th}$ day, the tumor was extracted, the tumor was weighed, and the tumor growth inhibition rate was calculated.

The results are shown in Table 1. RA16 can significantly inhibit tumor growth in human non-small cell lung cancer H460 transplanted tumor mice (inhibition rate 54.3%).

TABLE 1

Inhibition rates of RA16 on tumor growth in tumor-bearing mice

| | Group | |
|---|---|---|
| | G1 Negative Control (Normal Saline) | G2 RA16 Group |
| Inhibition Rate (%) | — | 54.26% |

Embodiment 5: Inhibitory Effect of RA16-EPI Adduct on Human Non-Small Cell Lung Cancer (In Vivo)

Figure 5:
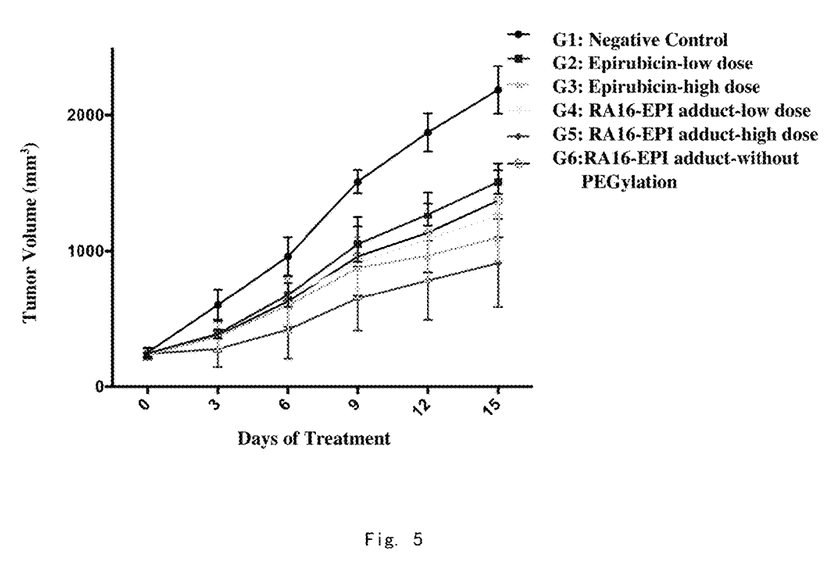
FIG. 5: A tumor growth curve for evaluating the efficacy of the RA16-EPI adduct or epirubicin (EPI) alone on tumor growth in tumor-bearing mice.

In order to clarify the effect of the nucleic acid aptamer RA16-EPI adduct on the growth of human non-small cell lung cancer solid tumors, the inventors used model mice that were injected with human non-small cell lung cancer H460 cells and constructed with a subcutaneous tumor as experimental subjects (initial mean tumor volume was 200-300 mm$^3$). They were randomly divided into 6 groups, each of which had 5 tumor-bearing mice. One group served as a negative control group (0.1 ml of normal saline was injected intravenously on the $0^{th}$, $7^{th}$, and $14^{th}$ days respectively); and the other 5 groups served as treatment groups (different doses of drugs were given every week, and the administration manners and doses are shown in Table 2.). Every 2 days, the tumor diameter of the tumor-bearing mice was measured, the tumor volume was calculated, and the tumor growth curves were drawn (FIG. 5). On the $16^{th}$ day, the tumor was extracted, the tumor was weighed, and the tumor growth inhibition rate was calculated.

The results are shown in Table 3. The RA16-EPI adduct can inhibit tumor growth in human non-small cell lung cancer H460 transplanted tumor mice more significantly than RA16 or EPI alone (the inhibition rate of high-dose group was 64.38%).

At the same time, the experimental results also indicate that PEGylation can increase the acting time of the adduct, and the therapeutic effect is increased by 50% compared with that of the RA16-EPI adduct without PEG modification, so the clinical application value is better.

TABLE 2

Specific administration manners when evaluating effect of RA16-EPI adduct in tumor-bearing mice

| Group | Drug | Administration Manner |
|---|---|---|
| G1 | Negative Control (Normal Saline) | 1-16 days, 0.1 ml/week, intravenous injection, a total of 3 times |
| G2 | Epirubicin (EPI, low dose) | 1-16 days, 0.5 mg/kg/week, intravenous injection, a total of 3 times |
| G3 | Epirubicin (EPI, high dose) | 1-16 days, 1.5 mg/kg/week, intravenous injection, a total of 3 times |
| G4 | RA16-EPI adduct (low dose) (PEGylated) | 1-16 days, EPI: 0.5 mg/kg/week, a total of 3 times, RA16:EPI (molar ratio) = 1:8, intravenous injection |
| G5 | RA16-EPI adduct (high dose) (PEGylated) | 1-16 days, EPI: 1.5 mg/kg/week, a total of 3 times, RA16:EPI (molar ratio) = 1:8, intravenous injection |
| G6 | RA16-EPI adduct (without PEGylation) | 1-16 days, EPI: 1.0 mg/kg/week, a total of 3 times, RA16:EPI (molar ratio) = 1:8, intravenous injection |

TABLE 3

Inhibition rate of tumor growth after administration of RA16-EPI adduct in each group

| | Group | | | | |
|---|---|---|---|---|---|
| | G2 Epirubicin (EPI, low dose) | G3 Epirubicin (EPI, high dose) | G4 RA16-EPI adduct (low dose) (PEGylated) | G5 RA16-EPI adduct (high dose) (PEGylated) | G6 RA16-EPI adduct (w/o PEGylation) |
| Tumor Weight (g) | 2.65 ± 0.21 | 1.97 ± 0.38 | 2.27 ± 0.21 | 1.33 ± 0.24 | 2.50 ± 0.26 |
| Inhibition Rate (%) | 28.76% | 47.13% | 39.07% | 64.38% | 32.80% |

Inhibition rate (%) = (The average tumor weight of the control group − The average tumor weight of the treatment group)/The average tumor weight of the control group × 100%

All documents mentioned in the present invention are incorporated herein by reference, just as each document is cited separately as a reference. In addition, it should be understood that various modifications and changes may be made to the present invention without departing from the scope of the teachings of the present invention, and these equivalent forms also fall within the scope defined by the claims appended hereto.

What is claimed is:

1. A pharmaceutical composition for treating a non-small cell lung cancer comprises a nucleicacid aptamer, an antitumordrug linked, coupled or polymerized with the nucleic acid aptamer, and a pharmaceutically acceptable carrier, wherein, the nucleicacid aptamer is:
    (1) a ribonucleic acid aptamer having a nucleotide sequence as shown in SEQ ID NO: 1; or

---

SEQUENCE LISTING

```
<160> NUMBER OF SEQ ID NOS: 3

<210> SEQ ID NO 1
<211> LENGTH: 83
<212> TYPE: RNA
<213> ORGANISM: Artificial Sequence
<220> FEATURE:
<223> OTHER INFORMATION: It is synthesized.

<400> SEQUENCE: 1
gggagagaac aaugaccugc ggugccaagc cgucggguua uguugaucuc cacaaggacg      60
agugcauugc aucacgucag uag                                             83

<210> SEQ ID NO 2
<211> LENGTH: 83
<212> TYPE: RNA
<213> ORGANISM: Artificial Sequence
<220> FEATURE:
<223> OTHER INFORMATION: It is synthesized.

<400> SEQUENCE: 2
gggagagaac aaugaccugu ugcaagcgcg ucgguaauuc gcgcacaugg caggcuucug      60
agugcauugc aucacgucag uag                                             83

<210> SEQ ID NO 3
<211> LENGTH: 103
<212> TYPE: DNA
<213> ORGANISM: Artificial Sequence
<220> FEATURE:
<223> OTHER INFORMATION: It is synthesized

<400> SEQUENCE: 3
cactaatacg actcactata gggagagaac aatgacctgc ggtgccaagc cgtcgggtta     60
tgttgatctc cacaaggacg agtgcattgc atcacgtcag tag                       103
```

(2) a ribonucleic acid aptamer having a nucleotide sequence complementary to the nucleotide sequence as shown in SEQ ID NO: 1; or
(3) a ribonucleic acid aptamer having 80% or more identity with the nucleotide sequence shown in SEQ ID NO: 1, or
(4) a ribonucleic acid aptamer having a nucleotide sequence complementary to 80% or more with the nucleotide sequence as shown in SEQ ID NO: 1.

2. The pharmaceutical composition according to claim 1, characterized in that the antitumor drug is a tumor-inhibiting chemotherapeutic drug, a tumor-inhibiting nucleic acid, or a tumor-inhibiting protein.

3. The pharmaceutical composition according to claim 2, characterized in that the chemotherapeutic drug includes, epirubicin, doxorubicin, carboplatin, cisplatin, paclitaxel, docetaxel and gemcitabine.

4. The pharmaceutical composition according to claim 3, characterized in that the chemotherapeutic drug is epirubicin, and the ribonucleic acid aptamer is adducted with epirubicin to form an adduct, the molar ratio of the ribonucleic acid aptamer to the epirubicin in the adduct being 1:(2-20).

5. The pharmaceutical composition according to claim 4, characterized in that the molar ratio of the ribonucleic acid aptamer to the epirubicin in the adduct is 1:(4-12).

6. The pharmaceutical composition according to claim 4, characterized in that the molar ratio of the ribonucleic acid aptamer to the epirubicin in the adduct is 1:(7-9).

7. The pharmaceutical composition according to claim 1, characterized in that the ribonucleic acid aptamer is a modified ribonucleic acid aptamer.

8. The pharmaceutical composition according to claim 7, characterized in that the modified ribonucleic acid aptamer is:

a modified ribonucleic acid aptamer obtained by linking a ribonucleic acid aptamer to PEG;

a ribonucleic acid aptamer embedded in a PEG-liposome mixture;

a nucleic acid aptamer with 2'F modified U and C bases;

a nucleic acid aptamer with 2'OMe modified bases; or a biotin modified nucleic acid aptamer.

* * * * *